United States Patent [19]

Ruszala

[11] 4,434,298

[45] Feb. 28, 1984

[54] OXYDEHYDROGENATION OF ISOBUTYRIC ACID AND ITS LOWER ALKYL ESTERS

[75] Inventor: Ferdinand A. Ruszala, Columbus, Ohio

[73] Assignee: Ashland Oil, Inc., Ashland, Ky.

[21] Appl. No.: 319,172

[22] Filed: Nov. 9, 1981

[51] Int. Cl.$^3$ .................... C07C 51/377; C07C 57/05; C07C 67/317; C07C 69/54
[52] U.S. Cl. .................................. 562/599; 560/214; 502/338
[58] Field of Search ...................... 562/599; 560/214; 252/472

[56] References Cited

U.S. PATENT DOCUMENTS 3,845,156  10/1974  Farha ................................. 252/437
3,948,959  4/1976  Cavaterra et al. ................. 562/599

FOREIGN PATENT DOCUMENTS 2438464  2/1975  Fed. Rep. of Germany ...... 562/599

*Primary Examiner*—Vivian Garner
*Attorney, Agent, or Firm*—John F. Jones

[57] ABSTRACT

Isobutyric acid or a lower alkyl ester thereof is oxidatively dehydrogenated in the vapor phase producing the corresponding $\alpha,\beta$-olefinically unsaturated derivative by contact with a heterogeneous catalyst in the presence of molecular oxygen. The catalyst is composed of the calcined mixture of salts of titanium and iron.

3 Claims, No Drawings

OXYDEHYDROGENATION OF ISOBUTYRIC ACID AND ITS LOWER ALKYL ESTERS

BACKGROUND OF THE INVENTION

1. Field of the Invention

This invention relates to the conversion of isobutyric acid or its equivalents and lower alkyl esters thereof correspondingly to methacrylic acid or its equivalent and lower alkyl esters thereof.

2. Description of the Prior Art

There exists considerable prior art relating to the oxydehydrogenation of the lower saturated aliphatic monocarboxylic acids to produce the corresponding $\alpha,\beta$-olefinically unsaturated acids. Early work in the area involved thermal, vapor phase oxydehydrogenation of the saturated aliphatic carboxylic acid in the presence of oxygen and iodine. This approach has not been particularly successful from a commercial standpoint. This is understandably so inasmuch as iodine is costly, exhibits extreme corrosivity properties and poses considerable problems in realizing complete recovery of the comparatively large amounts thereof required in the process. The heterogeneous catalytic method for oxydehydrogenation according to the prior art appears to be the more attractive route to the commercial production of olefinically unsaturated acids. The prior art heterogeneous oxydehydrogenation catalysts useful for this purpose include some heteropoly acids, such as phosphomolybdic acid, optionally with tungsten and/or vanadium. Another type of catalyst included in the prior art is iron phosphate.

Iron phosphate subjected to calcination exists in several crystalline phases or species. It is not known at this time which species is or are catalytically active. There is evidence that the presence of certain extrinsic metal components in the catalyst preparation serves to facilitate the formation of the active catalyst. For instance, U.S. Pat. No. 3,948,959 discloses that an alkali or alkaline earth metal can be the extrinsic metal component for this purpose.

SUMMARY OF THE INVENTION

In accordance with this invention, a catalytic process is provided for the oxidative dehydrogenation of a saturated aliphatic monocarboxylic acid or lower ester thereof, such as isobutyric acid or methyl isobutyrate, to the corresponding $\alpha,\beta$-olefinically unsaturated derivative thereof, such as methacrylic acid or methyl methacrylate. The process of this invention comprises contacting a heterogeneous catalyst at a temperature in the range of from 300°–1000° C. with a mixture of the saturated aliphatic monocarboxylic acid and molecular oxygen, said catalyst being the calcined combined oxides of titanium and iron. Although the exact structure and nature of the catalyst is not known, the catalyst may be conveniently defined by the gram-atom empirical formula $Fe_aTi_bO_x$ wherein a is 0.25-3, b is 0.25-1, and x represents the number of oxygens required to satisfy the uncombined positive valences of the other elements shown in the formula.

DESCRIPTION OF THE PREFERRED EMBODIMENT

There are a number of techniques which can be used for preparing the catalyst useful in the process of this invention. Of these, the more facile methods involve preparing the integral catalyst composition prior to calcination. This can be readily and conveniently accomplished by the so-called slurry method in which metal salts, either soluble or not, are mixed in a liquid medium, such as water, the water is removed and the resulting solid is calcined producing the desired catalyst. Suitable calcination temperatures range from 400°–1000° C. Applicable periods of calcination range from 2–30 hours although longer periods can be used without adverse results.

The use of a support or carrier for the catalyst is within the scope of this invention. The support can be included in the slurry preparation of the catalyst mentioned above. Useful carriers include colloidal silica or any other form of silica, alumina, pumice, zirconia, quartz, carbon, silicon carbide, etc.

The process of this invention can be carried out using the catalyst in the form of a fluidized bed reactor, a stirred tank reactor or in a fixed bed or packed bed reactor or any combination of these types of reactors. Because of the convenience associated with the use of a fixed bed reactor in a small scale operation, such a reactor will be exemplified herein. In the preferred mode of operation the feed to the reactor comprises a pre-heated gaseous mixture of the saturated aliphatic monocarboxylic acid, optionally acetone, molecular oxygen, steam and inert diluent gas. A pre-heat temperature in the range of about 300° to 350° C. is customarily used. The oxydehydrogenation reaction can be carried out in the range of from 300° to 500° C. More generally a temperature of from 375° to 475° C. provides for optimum processing.

The mole ratio of molecular oxygen to carboxylic acid is from 0.5 to 1.5 and more preferably from 0.7 to 0.75 in the case where the carboxylic acid is isobutyric acid per se. Although steam is not necessary for the reaction, its presence is desirable in the feed because it is believed to act beneficially as a heat sink and in minimizing combustion of the carboxylic acid to undesirable waste products. The mole ratio of water to the carboxylic acid in the feed should be from about 8 to 20. The optimum ratio is from 12 to 15.

Another important parameter is the concentration of the organic reactant in the feed. The organic reactant carboxylic acid or ester should be present in the feed in from 0.1 to 20 mole percent. From the standpoint of achieving a resonable throughput combined with an acceptable yield, the concentration of the reactant in the feed is from about 3–6 mole percent. Concentration of reactant in the feed is controlled to a large degree by the amount of inert gas or diluent present. The preferred inert gas or diluent is nitrogen. Although other inert gases such as carbon dioxide, helium, argon, and the like are suitable. Air is a very convenient source of oxygen plus inert diluent.

Another important parameter is contact time in the process of this invention. Contact or reaction time is defined for the purpose of this invention as the catalyst volume divided by the volume of gas feed per second at the reaction temperature. The catalyst volume is the bulk volume occupied by the catalyst in the reactor. The term catalyst in this sense not only includes the elements shown in the empirical formula above, but also includes any support material if it is present. Accordingly, reaction times can range from 0.05 to 3.0 seconds and more generally in the order of from 0.1 to 1.0 second. The reaction is preferably carried out at or near atmospheric pressure although the use of higher pressures up to about 10 atmospheres is contemplated.

The process of this invention is further illustrated in the following specific examples.

EXAMPLE I

The slurry method was used to prepare a titanium-iron oxide catalyst. To a solution of 20.20 g. of Fe(NO$_3$)$_3$.9H$_2$O in 100 ml. of deionized water were added 12 g. of 5 micron TiO$_2$. The resulting slurry was dried at 120° C. for one day. The resulting solid was calcined for 2 days at 900° C. The final catalyst was found by analysis to conform to the empirical formula $$Fe_2Ti_{11}O_5$$

EXAMPLE II

This example illustrates the use of the catalyst described in Example I in the oxydehydrogenation of isobutyric acid to produce methacrylic acid. The procedure consisted of feeding a pre-heated mixture of isobutyric acid, oxygen, nitrogen, acetone and water through a stainless steel tube of ½" O.D. (3/8' I.D.) and approximately 2" in length containing 0.5 g. of the catalyst in a packed bed maintained at the reaction temperature.

The pre-heater consisted of a length of stainless steel tubing similar to the reactor but packed with glass beads. The condensed organic product was separated from the water, collected and analyzed by the internal standard method of gas chromatography.

Selectivity to methacrylic acid represents the mole ratio of methacrylic acid found in the reaction effluent to that of the isobutyric acid consumed in the reaction.

The feed to the reactor consisted of isobutyric acid:acetone:water:air in the amounts 336 cc:55 cc:1080 cc:20 standard cc/min. At a rate of 5.7 cc/hour. Various reaction temperatures were used and the conditions and results are given in the following table.

TABLE

|  | A | B | C | D | E | F |
| --- | --- | --- | --- | --- | --- | --- |
| Reaction Temp., °C. | 417 | 417 | 435 | 451 | 450 | 451 |
| % Conversion | 28.46 | 31.76 | 30.73 | 35.45 | 32.57 | 37.60 |
| % Selectivity | 45.72 | 45.01 | 46.01 | 45.29 | 44.09 | 30.34 |

We claim:
1. In a process for the catalytic conversion of isobutyric acid or a lower alkyl ester thereof to the corresponding α,β-olefinically unsaturated derivative of oxydehydrogenation wherein a catalyst is contacted with a gaseous feed stream containing said acid or ester and molecular oxygen at a temperature between about 300° and 1000° C., the improvement comprising using as catalyst a material having the gram-atom empirical formula Fe$_a$Ti$_b$O$_x$ wherein a is 0.25 to 3, b is 0.25 to 1, and x represents a number determined by satisfying the sum of the unshared positive valences of the other elements shown in the formula.
2. The process of claim 1 wherein isobutyric acid is converted to methacrylic acid.
3. The process of claim 2 wherein the catalyst has the gram-atom empirical formula Fe$_2$Ti$_{11}$O$_5$.

* * * * *